(12) United States Patent
Watanabe et al.

(10) Patent No.: US 7,689,369 B2
(45) Date of Patent: Mar. 30, 2010

(54) PROBLEM DIAGNOSIS METHOD AND PROBLEM REPAIR METHOD FOR LASER DEVICE

(75) Inventors: Akira Watanabe, Okayama (JP); Tadashi Okuno, Okayama (JP); Hiroshi Tsugita, Okayama (JP); Tetsumi Sumiyoshi, Tokyo (JP); Hitoshi Sekita, Tokyo (JP)

(73) Assignee: Cyber Laser Inc., Tokyo (JP)

( * ) Notice: Subject to any disclaimer, the term of this patent is extended or adjusted under 35 U.S.C. 154(b) by 833 days.

(21) Appl. No.: 11/436,817

(22) Filed: May 18, 2006

(65) Prior Publication Data

US 2006/0274794 A1 Dec. 7, 2006

(30) Foreign Application Priority Data

May 20, 2005 (JP) ............................. 2005-147737

(51) Int. Cl.
*G01B 3/44* (2006.01)
*G01B 3/52* (2006.01)
*G01B 5/30* (2006.01)
(52) U.S. Cl. .......................................... 702/34; 702/35
(58) Field of Classification Search ............. 702/34–36, 702/40, 182, 59, 183–185, 179, 181; 700/108, 700/110; 356/237.1, 239.2; 706/45, 52
See application file for complete search history.

(56) References Cited

U.S. PATENT DOCUMENTS

| | | | |
|---|---|---|---|
| 6,631,153 B2 * | 10/2003 | Sumiyoshi et al. | 372/75 |
| 7,126,232 B2 * | 10/2006 | Imahara et al. | 257/798 |
| 2002/0126724 A1 * | 9/2002 | Tsunekane et al. | 372/69 |
| 2006/0050223 A1 * | 3/2006 | Umetsu | 349/192 |
| 2007/0081105 A1 * | 4/2007 | Park et al. | 349/22 |
| 2007/0112529 A1 * | 5/2007 | Bigarre et al. | 702/59 |

FOREIGN PATENT DOCUMENTS

JP 8-97778 4/1996

* cited by examiner

*Primary Examiner*—Michael P Nghiem
(74) *Attorney, Agent, or Firm*—Pearne & Gordon LLP

(57) ABSTRACT

A problem diagnosis method and problem repair method for a laser device are provided. The method includes measuring the intensity of scattered light generated by an optical part inside the laser device; referring to data indicating a temporal change in the scattered light predicted under predetermined operating conditions of the laser device, and predicting the seriousness of the problem from the intensity of scattered light; and determining what kind of maintenance work is necessary based on the seriousness of the problem. Additionally, the seriousness of the problem in the optical part can be predicted by executing fuzzy logic based on membership functions defining the relationship between scattered light intensity and the seriousness of problems of optical parts.

7 Claims, 14 Drawing Sheets

| OPERATIONAL MODE | PULSE |
|---|---|
| IDLER ENERGY | 10 (Mj) |
| PULSE WIDTH | 300 (µs) |
| REPETITIONS | 30 (Hz) |

FIG. 7

| | | LD CURRENT | | |
|---|---|---|---|---|
| | | NORMAL | GRAY | MALFUNCTION |
| SCATTERED LIGHT INTENSITY | NORMAL | NO PROBLEMS | CAUTION | REPAIR |
| | GRAY | CAUTION | WARNING | REPAIR |
| | MALFU-NCTION | WARNING | WARNING | REPAIR |

FIG. 8

| LD CURRENT | ANTECEDENT PART | CONSEQUENT PART |
|---|---|---|
| NORMAL |  |  |
| GRAY |  |  |
| MALFU-NCTION |  |  |

PROBLEM DIAGNOSIS METHOD AND PROBLEM REPAIR METHOD FOR LASER DEVICE

BACKGROUND OF THE INVENTION (1) Field of the Invention

The present invention relates to a problem diagnosis method and problem repair method for a laser device and programs for carrying out these methods, and particularly relates to methods for automatically diagnosing and repairing problems in laser devices caused by deterioration of optical parts and the like. For the purposes of this application, the expression "laser device" shall refer broadly to devices that use laser beams for medical, industrial or other applications, including laser treatment devices used in the medical field to perform therapy or surgery on affected parts of the body, or laser processing devices used for processing materials and the like in the industrial field. Additionally, the expression "problem" shall refer generally to situations in which malfunctions or deteriorations occurring in the components of a laser device such as optical parts impairs the ability of the components to perform their intended functions.

(2) Description of the Related Art

In the medical field, laser devices are widely used for the purposes of treatment or diagnosis. Carbon dioxide lasers and flash lamp-pumped neodium (Nd) ion-doped yttrium aluminum garnet (YAG) lasers are often used for cutting soft tissues and performing hemostasis. Additionally, discharge-pumped argon fluoride (ArF) excimer lasers are used to perform corrective surgery on the cornea of the eye. Furthermore, erbium (Er)-doped YAG lasers are used for boring into the hard tissues of the teeth.

Laser devices including laser devices for medical applications have a warm-up time which is required to raise the device overall to a standard temperature in order to stabilize the output optical power. A mechanism may be provided to detect the temperature and flow rate of coolant, and leakage of electric current in the power supply of the excitation lamp after the warm-up time has passed using various sensors in order to find any anomalies in the operation of the laser device, and activating an interlock to stop the laser device if, for example, the measured values are below a predetermined threshold value. A system for detecting various types of data relating to a laser device and stopping the device if an anomaly has been found to occur in the device is described, for example, in Japanese Patent Application, First Publication No. H8-97778.

When an operational anomaly occurs in an anomaly detecting system such as described above, the user is notified that the device is in an anomalous state of operation by a warning tone or a warning display on a screen adjoined to the laser device. The user then contacts a maintenance worker to perform inspections and repairs, and waits until the maintenance worker arrives.

Additionally, in many models, when there is a decrease in output optical power due to deterioration of the optical parts but within such a range that it is not judged to be an operational anomaly, the input voltage is increased to compensate for the reduction in optical output, as a result of which the optical part which is the cause of the decreased output can be overloaded and thereby irretrievably damaged. The user often only becomes aware of a malfunction in a device, and can therefore only request repair by a maintenance worker, after the problem has already had an adverse effect on medical or processing work With the above anomaly detecting methods, a maintenance worker is not contacted until an anomaly occurs in the laser device, so that discovery of a malfunction can be delayed and the laser device can be heavily damaged, thus requiring a lot of time to perform repairs. For example, if a laser device used for a medical application is severely damaged, it will not be possible to perform the medical treatments until the damage is repaired. Additionally, when a malfunction occurs, the user is not able to perform repairs and must contact a maintenance worker and wait until the maintenance worker finishes the repairs, thus giving rise not only to repair costs but also to lost opportunity costs as the laser device is left unused during the wait.

BRIEF SUMMARY OF THE INVENTION

The present invention was made with the purpose of resolving the above-described problems, and offers a problem diagnosis method for a laser device capable of discovering problems such as malfunctions in laser devices at an early stage, thus shortening the time required for maintenance work such as inspection and repair of the laser device. Additionally, the present invention offers a problem repair method for a laser device, for repairing malfunctions or deterioration of parts discovered by the above problem diagnosis method without the need to contact a maintenance worker, thus reducing the cost of repairs.

In order to achieve the above purpose, the problem diagnosis method or problem diagnosis program for a laser device according to the present invention involves measuring the intensity of scattered light generated by an optical part in the laser device; referring to data indicating a relationship between the intensity of scattered light under predetermined operating conditions of the laser device and the seriousness of the problem in the optical part, and predicting the seriousness of the problem from the intensity of scattered light; and determining what kind of maintenance work is necessary based on the seriousness of the problem.

Additionally, the problem diagnosis method or problem diagnosis program for a laser device according to the present invention can involve measuring the intensity of scattered light generated by an optical part in the laser device; referring to data indicating a temporal change in the scattered light predicted under predetermined operating conditions of the laser device to predict the seriousness of the problem in the optical part; and determining what kind of maintenance work is necessary based on the seriousness of the problem. Additionally, it can involve measuring other operational data indicating the operational state of the optical part aside from the intensity of scattered light; referring to data indicating a temporal change in the other operational data predicted under predetermined operating conditions of the laser device to predict the seriousness of the problem in the optical part; and determining what kind of maintenance work is necessary based on the seriousness of the problem derived from the intensity of scattered light and the seriousness of the problem derived from the other operational data.

Additionally, the problem diagnosis method or problem diagnosis program for a laser device according to the present invention can involve measuring the intensity of scattered light generated by an optical part in the laser device; executing fuzzy logic based on a membership function defining the relationship between the intensity of scattered light under predetermined operating conditions of the laser device and the seriousness of the problem in the optical part to predict the seriousness of the problem from the intensity of scattered light; and determining what kind of maintenance work is necessary based on the seriousness of the problem. Additionally, it can involve measuring other operational data indicating the operational state of the optical part in the laser device aside from the intensity of scattered light; executing fuzzy logic based on a membership function defining the relationship between the other operational data under predetermined operating conditions of the laser device and the seriousness of the problem in the optical part to predict the seriousness of the problem in the optical part; and determining what kind of maintenance work is necessary based on the seriousness of the problem derived from the intensity of scattered light and the seriousness of the problem derived from the other operational data.

Additionally, the problem diagnosis method or problem diagnosis program for a laser device according to the present invention can involve setting operational parameters of the laser device. When the operational parameters are set by a user, data indicating the temporal change in operational data such as scattered light intensity predicted under the operating environment of the laser device defined by said operational parameters are retrieved or generated. Additionally, one or a plurality of membership functions defining the relationship between operational data such as scattered light intensity under the operating environment of the laser device defined by said operational parameters and the seriousness of the problem in the optical part can be retrieved or generated. Furthermore, problem information obtained as a result of prediction or determination can be reported to a management center through a network. At the management center, a maintenance worker can be instructed to perform inspections or repairs based on the obtained problem information.

In a problem repair method or problem repair program for a laser device according to the present invention, when a laser device is determined to need repairs using the above-described problem diagnosis method or problem diagnosis program, the optical part is moved so as to change the position on which the laser beam is irradiated on the optical part in which the problem occurred. Additionally, said optical part can be moved until the intensity of scattered light generated by the optical part becomes equal to or less than a predetermined threshold value.

According to the present invention, the seriousness of a problem is predicted on the basis of the intensity of scattered light that has a correlation with changes in the surface state caused by material deterioration and the like, thus enabling the advancement of deterioration in the optical part to be recognized, and allowing the optical part to be repaired or replaced before a serious malfunction occurs, making the maintenance of the laser device easier and shortening the overall time required for maintenance work on the laser device.

According to the present invention, the seriousness of a problem is predicted by referring to data indicating the temporal change in the scattered light intensity predicted in predetermined operating environments, so that the probability of the seriousness of a problem in an optical part derived from the intensity of the scattered light can be checked based on the time of use of said optical part, thus enabling the seriousness of the problem of the optical part to be accurately predicted, and improving the reliability of the results of determination of maintenance work.

According to the present invention, the seriousness of a problem is predicted by executing fuzzy logic based on a membership function defining the relationship between the intensity of scattered light in predetermined operating environments and the seriousness of the problem in the optical part, thus enabling the seriousness of the problem in the optical part to be accurately predicted and improving the reliability of results of determination of maintenance work by expressing various empirical rules by means of the membership function.

According to the present invention, the seriousness of a problem is predicted by measuring other operational data indicating the operational state of the optical part and referring to data indicating the temporal change of said operational data, or executing fuzzy logic based on a membership function defining the relationship between said operational data and the seriousness of the problem in the optical part, so that the problem is predicted by combining the seriousness of the problem derived from the intensity of the scattered light and the seriousness of the problem derived from the other operational data, thus enabling the seriousness of the problem in the optical part to be accurately predicted and improving the reliability of the results of determination of maintenance work.

According to the present invention, the operational parameters of the laser are set, and data indicating the temporal change in operational data predicted under the operating environment of the laser device defined by the set operational parameters are retrieved or generated, or a membership function defining the relationship between said operational data under the operating environment of the laser device defined by the set operational parameters and the seriousness of the problem in the optical part is retrieved or generated, thus enabling the seriousness of a problem in a laser device to be predicted for various operating environments, so that more suitable maintenance work can be performed.

According to the present invention, the problem information can be reported to a management center through a network thus enabling the problem to be analyzed using a large-scale database, so that more suitable maintenance work can be performed.

According to the present invention, a maintenance worker at the management center is instructed to perform inspections or repairs based on the problem information, thus reducing the time needed from when the problem occurs until the laser device is repaired. Additionally, since a maintenance worker is notified by the management center of the problem information and analysis information relating to the problem, maintenance work on the laser device can be performed more efficiently.

According to the present invention, the optical part is moved so as to change the position at which the laser beam is irradiated on the optical part in which the problem occurred, thus enabling the laser device to be automatically repaired without contacting a maintenance worker, and reducing the number of times the laser device must be stopped for repairs while also reducing the repair cost.

According to the present invention, the optical part is moved until the intensity of scattered light generated by the optical part becomes equal to or less than a predetermined threshold value, thus enabling the optical part to be reliably moved until its position is reached at which the optical part provides a predetermined function, thereby improving the reliability of the repair of the laser device.

BRIEF DESCRIPTION OF THE DRAWINGS

FIG. 7 is a table showing an example of operational parameters defining the operational environment of the laser device.

FIG. 8 is a table showing an example of a determination pattern concerning the need for maintenance work.

DETAILED DESCRIPTION OF THE INVENTION

Herebelow, preferred embodiments of the problem diagnosis method and problem repair method for a laser device according to the present invention shall be explained in detail with reference to the attached drawings.

Figure 1:
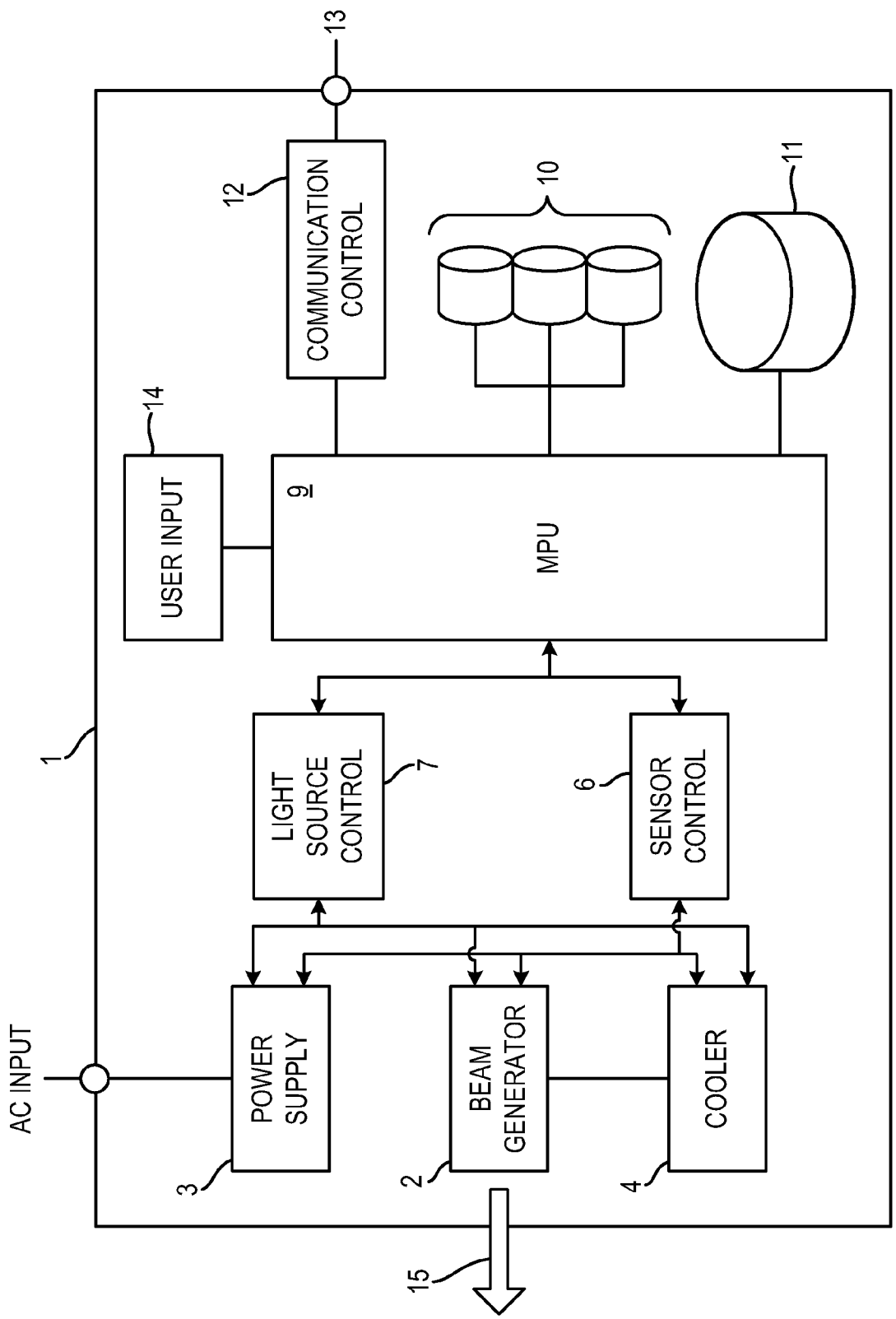
FIG. 1 is a schematic view showing an example of the structure of a laser device used in the present invention.

FIG. 1 is a schematic view showing an example of the structure of a laser device used in the present invention. The laser device mainly comprises a beam generator 2, a power supply portion 3, a cooler 4 and a data managing device. The data managing device comprises a sensor control portion 6, a light source control portion 7, an MPU (microprocessor unit) 9, a memory 10, a high-capacity memory device 11 and a communication control portion 12. The power supply portion 3 supplies electrically driven parts of the laser device with electric power via electric lines that are not shown. The beam generator 2 outputs a laser beam 15. The cooler 4 exchanges heat generated in the beam generator 2.

The MPU 9 controls the operation of the sensor control portion 6 and the light source control portion 7. The sensor control portion 6 controls the measurement start times, measurement intervals and measurement time widths of sensors provided in the power supply portion 3, the beam generator 2 and the cooler 4, and processes the operational data that is obtained. That is, the sensor control portion 6 integrates the time waveform of the optical output measured by a high-speed light sensor to calculate the pulse energy, and also calculates the average value of the optical output from a set number of samples. The light source control portion 7 controls the operation of the power supply portion 3, cooler 4 and the like so as to operate the beam generator 2 based on operational parameters set by using the user input portion 14. This series of control operations can be performed by the MPU 9 by executing a program recorded in the memory 10 or the high-capacity memory device 11. While the operational data obtained from the sensors is stored in the memory 10, the MPU 9 and the memory 10 are capable of high-speed data transfer by which they are able to obtain operational data in real-time.

The operational data detected by the sensors is first stored in the memory 10. Some or all of the operational data stored in the memory 10 is transferred and recorded in the high-capacity memory device 11, after which new operational data may be stored in the memory 10. Furthermore, some or all of the operational data recorded in the high-capacity memory device 11 may be sent through a communication control portion 12 to a management center connected via an external communication network 13. The high-capacity memory device 11 may, for example, be a removable recording medium such as, for example, a magnetic recording device, in which case the maintenance worker can collect the recording medium to analyze the operational data. The communication control portion 12 may be connected to the communication network through cables, or may be connected by wireless.

Figure 2:
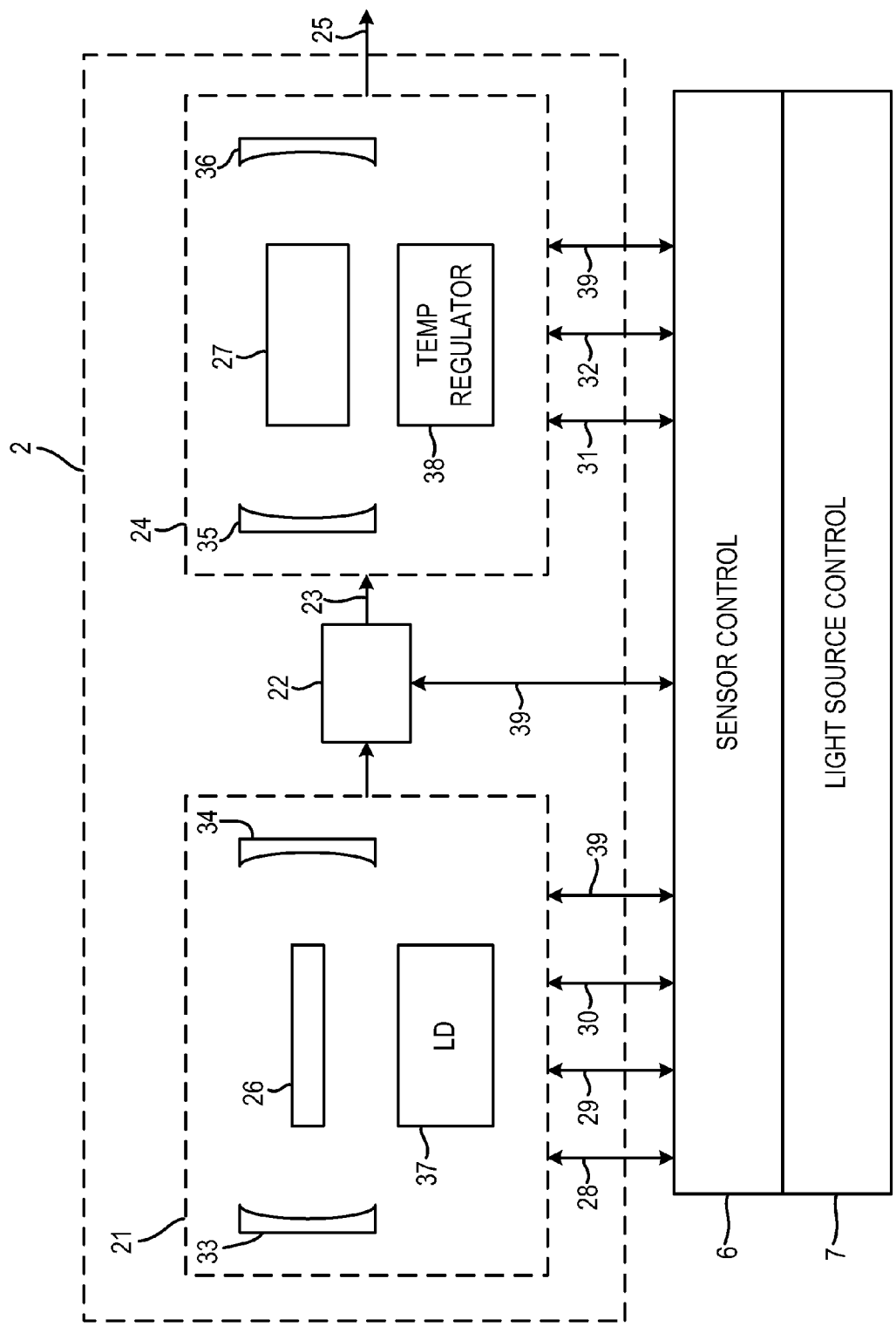
FIG. 2 is a schematic view showing an example of the structure of a beam generator used in the present invention.

Next, the beam generator 2 shall be explained. FIG. 2 is a schematic view showing an example of the structure of a beam generator used in the present invention. The beam generator 2 mainly comprises an LD-pumped solid-state laser 21 and a non-linear wavelength converting means 24. An LD-pumped solid-state laser 21 has a basic structure consisting of a laser crystal 26 which is the pumping means, an LD 37, a rear mirror 33 and an output mirror 34. A laser beam outputted from an LD-pumped solid-state laser 21 is a fundamental beam 23 that is coupled to the non-linear wavelength converting means 24 by a beam adjusting means 22. The beam adjusting means 22 may comprise a convergent lens and an optical isolator for the fundamental beam 23. The non-linear wavelength converting means 24 is an optical parametric oscillator (OPO), comprising a non-linear optical crystal 27, an OPO input mirror 35 and an OPO output mirror 36. The OPO resonator may have a linear resonator structure, or alternatively may have a ring-type structure with four OPO mirrors.

The OPO generates a signal beam and an idler beam based on the fundamental beam 23. When an Nd:YAG crystal is used as the laser crystal and a periodically poled lithium niobate (PPLN) crystal is used as the non-linear optical crystal 27, a 1.66 μm signal beam and a 2.94 μm idler beam can be generated from a 1.06 μm fundamental beam by controlling the PPLN temperature using a temperature regulator 38. The output beam 25 includes one, two or all three of the fundamental beam, the signal beam and the idler beam.

The LD-pumped solid-state laser 21 is provided with a photodetector for detecting the temporal waveform of the fundamental beam 23, a photodetector for detecting the temporal waveform of the output beam of the LD 37, and sensors for measuring the temperature and flow rate of coolant used for exchanging heat in the laser medium 26 and the LD 37. These sensors are controlled by the sensor control portion 6. Additionally, the sensor control portion 6 inputs data obtained from the sensors via a fundamental beam output data channel 28, an LD output data channel 29, a coolant data channel 30 and the like. Furthermore, the non-linear wavelength converting means 24 comprises a photodetector for detecting the temporal waveform of the output beam 25 including the idler beam or signal beam which is the wavelength-converted beam, and sensors for detecting at least one of the temperature, electric current or voltage of the temperature regulator 38. These sensors are also controlled by the sensor control portion 6. The sensor control portion 6 inputs data obtained by the sensors via a wavelength-converted output data channel 31, a temperature data channel 32 and the like.

Additionally, a scattered light sensor is provided in the vicinity of one or more optical parts in the beam generator 2 for measuring the intensity of scattered light generated when the laser beam is illuminated. The sensor control portion 6 controls these scattered light sensors and inputs data obtained by these sensors via a data channel 39. Additionally, as will be explained below, the structure may be such as to transmit control signals outputted in order to move the optical parts during repair of a problem through the data channel 39.

Figure 3:
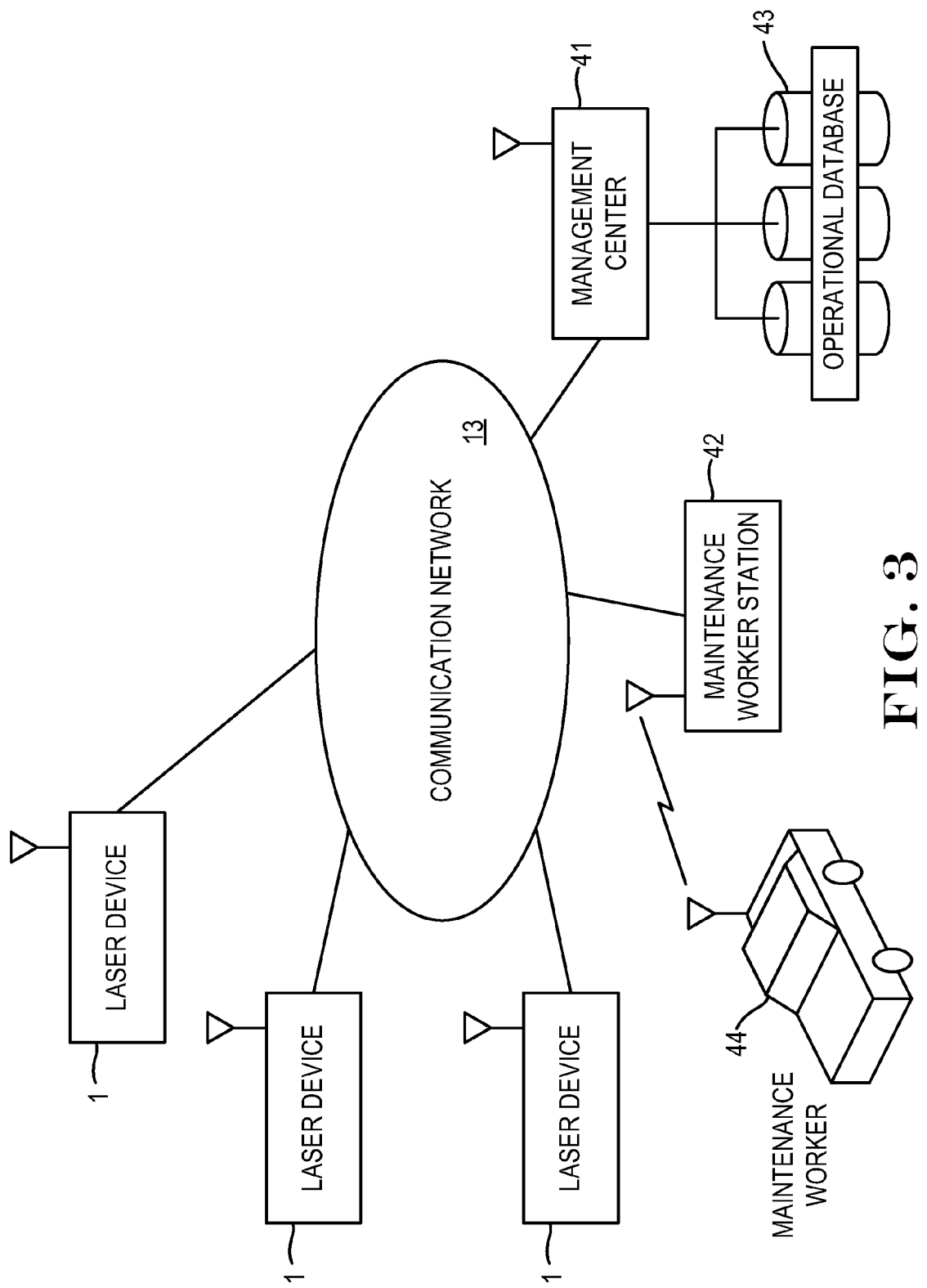
FIG. 3 is a schematic view showing an example of the structure of a network system used in the present invention.

Next, a network system for carrying out problem diagnosis and problem repair shall be explained. FIG. 3 is a schematic view showing an example of the structure of a network system used in the present invention. Laser devices 1 are connected to a communication network 13 via communication control portions provided on each. A management center 41 and a maintenance worker station 42 are connected to this communication network. This communication network 13 should preferably be constructed, for example, on the internet.

Operational data detected by the laser devices are transmitted to the management center 41, then recorded in the operational database 43. The operational database 43 is divided according to the area where the laser device 1 is set and the type of laser device, and is shown as a plurality of recording devices in order to express this. The operational database 43 records operational data relating to each laser device. The management center 41 analyzes operational data that is newly transmitted based on recorded data to predict the operational states of the laser devices, thus enabling the most suitable kind of maintenance work to be determined.

Upon detecting an operational anomaly in any of the laser devices 1, the management center 41 identifies the area where the anomaly occurred, and sends the maintenance worker station 42 an anomaly code indicating the measures to be taken against the operational anomaly. A maintenance worker 44 who has received an anomaly code at the maintenance worker station 42 goes to the location of the laser device 1 carrying the parts necessary for inspection and repairs, and repairs or replaces the parts which are operationally defective. The maintenance worker 44 has communication means for communicating with the maintenance worker station during the maintenance work and is capable of receiving information about other laser devices in which operational anomalies have occurred while he has been working, so as to be able to immediately go to the location of the next laser device upon completion of the current maintenance work. In this case, a cellular phone or the like may be used as wireless communication means. Furthermore, since the network elements are coupled to various communication means, it is possible for staff to check the state of each others' maintenance work. As a result, a supervisor at the maintenance worker station 42 can check the state of work of the maintenance workers 44 to construct the most efficient maintenance worker management schedules in real-time.

Additionally, in the above network system, some of the functions of the laser devices may be replaced by personal computers (PC's). The functions of the sensor control portion 6, user input portion 14, MPU 9, memory 10, high-capacity memory device 11 and communication control portion 12 of the laser devices can be replaced by a PC. By using a PC, it is possible not only to manage data relating to laser devices, but also data relating to various medical tools capable of outputting an electronic signal among the medical tools used by a user, for example, on the medical scene. Additionally, the data may also be managed by a management center.

Figure 4:
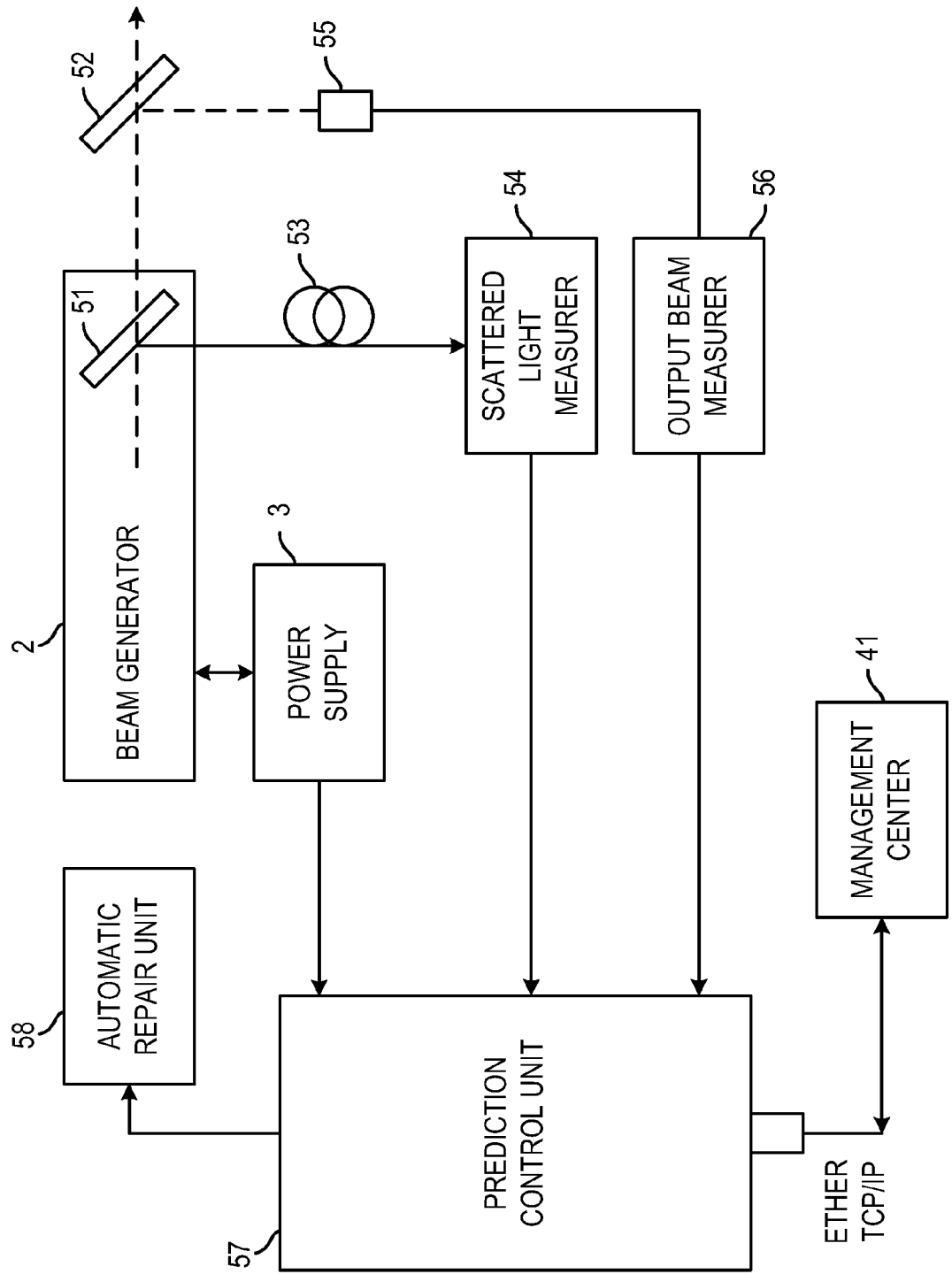
FIG. 4 is a schematic view showing the measurement of scattered light in an optical part using a scattered light sensor.

As mentioned above, various sensors are used in the present invention to detect the operational state of a laser device. FIG. 4 is a schematic view showing an example of the structure of a problem repair system. An optical part 51 is placed inside the beam generator 2 installed in a laser device, and an optical part 52 is placed outside. When a laser beam is incident on the optical part 51, light is scattered according to the surface state of the optical part. An optical fiber sensor 53 is composed, for example, of an optical fiber and a photodiode, and outputs an electrical signal that corresponds to the quantity of scattered light that is detected. A scattering light measurer 54 receives the output signal from the optical fiber sensor 53 and detects the intensity of scattered light. Additionally, the optical sensor 55 receives a laser beam that is partially reflected by the optical part 52 and outputs an electrical signal corresponding to the quantity of light. An output beam intensity measurer 56 receives the output signal from the optical sensor 55 as an input and detects the output beam intensity.

A prediction control unit 57 receives various signals relating to operational data from the various sensors, including a scattered light intensity signal outputted from the scattered light measurer 54 and an output beam intensity signal outputted from the output beam intensity measurer 56. Additionally, the prediction control unit 57 predicts the seriousness of the problem that has occurred in the optical part based on the operational data, and determines the maintenance work that is needed depending on the predicted seriousness of the problem. If it is found as a result of the determination that a problem has occurred in the optical part 51 and it is necessary to repair the optical part, a control signal is outputted to an automatic repair unit 58. The automatic repair unit 58 operates to repair the optical part 51 in accordance with the control signal.

Here, we shall describe a number of factors that cause increases in scattered light in optical parts. While the optical thin films used in optical parts are ideally considered to be devices that only transmit or reflect light and do not absorb light, in actuality, they do absorb some photonic energy. As the wavelength of a laser beam becomes shorter, the amount of photonic energy becomes larger, so that the absorbed photonic energy will cause the optical thin film to melt and disperse. The dispersed material causes the laser beam to scatter. Additionally, when the laser beam hits impurities that were introduced during manufacture, thermal absorption occurs, and this heat can cause the material of the optical parts to deteriorate and scatter the laser beam. Additionally, the laser irradiation can cause an electromagnetic field to be formed, thus attracting microparticles, or laser irradiation can cause an optical CVD effect, thus generating microparticles, and these microparticles can cause the laser light to scatter. Furthermore, the high energy of a laser beam can ionize and activate oxygen in the air, as a result of which volatile micromolecular gases and oxygen present in the laser device can bind together and form oxides, and these oxides can accumulate on the surfaces of optical parts and cause scattering of laser beams.

Regardless of which of the above factors is the cause of the scattered light, when the surface state of the optical parts related to laser oscillation changes, losses can occur in the laser beam, and in the worst case, laser oscillation can be halted altogether. Additionally, when the film properties change due to the above factors and cause the absorption of the laser beam to increase, the deteriorated portions can be a source of heat and cause the optical parts to be thermally damaged. Since scattered light can be expected to increase as this deterioration of optical parts progresses, it is possible to predict the level of deterioration of the optical parts by measuring the scattered light in the vicinity of the optical parts.

Figure 5:
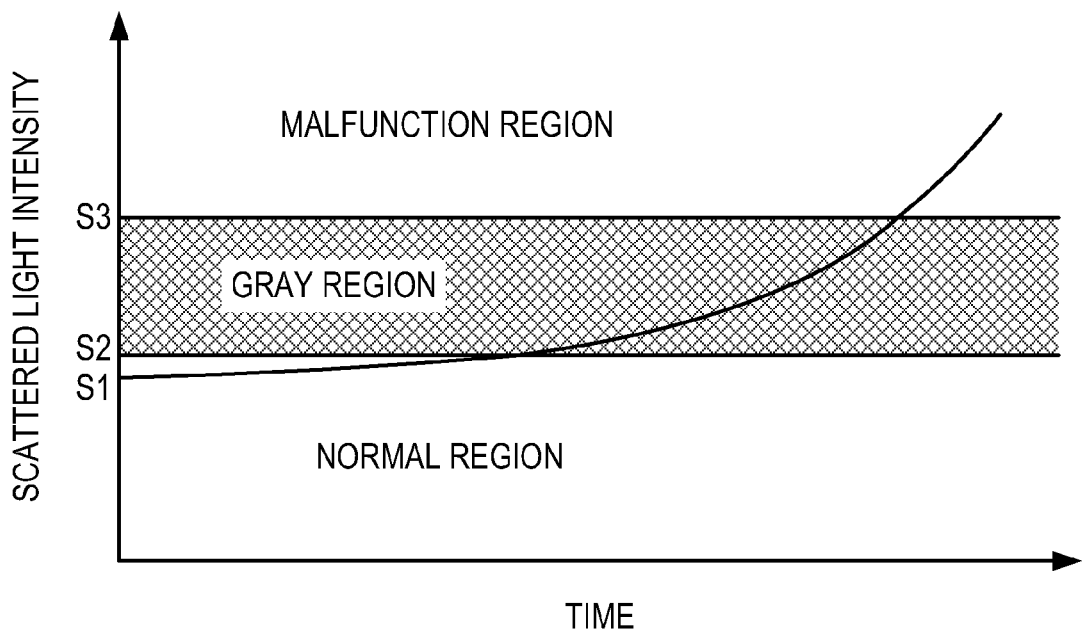
FIG. 5 is a diagram showing the temporal change in the scattered light intensity.

Next, methods of predicting the seriousness of a problem in an optical part shall be explained. According to a first prediction method, the seriousness of the problem is predicted by referring to data indicating the temporal change in operational data such as scattered light intensity predicted under a predetermined operational environment of the laser device. FIG. 5 is a diagram showing the temporal change in the scattered light generated in an optical part. When an optical part that generates scattered light of intensity S1 at the time of delivery is continuously subjected to irradiation by a laser beam, changes in the surface state caused by the gradual deterioration of the optical part over time will make the intensity of the scattered light generated from the optical part increase. While a scattered light intensity of up to S2 will be determined to be normal, a scattered light intensity exceeding S3 will be determined as indicating a malfunction. The intensities S2 and S3 used as the criteria here are selected, for example, on the basis of experimental data or the like.

Figure 6:
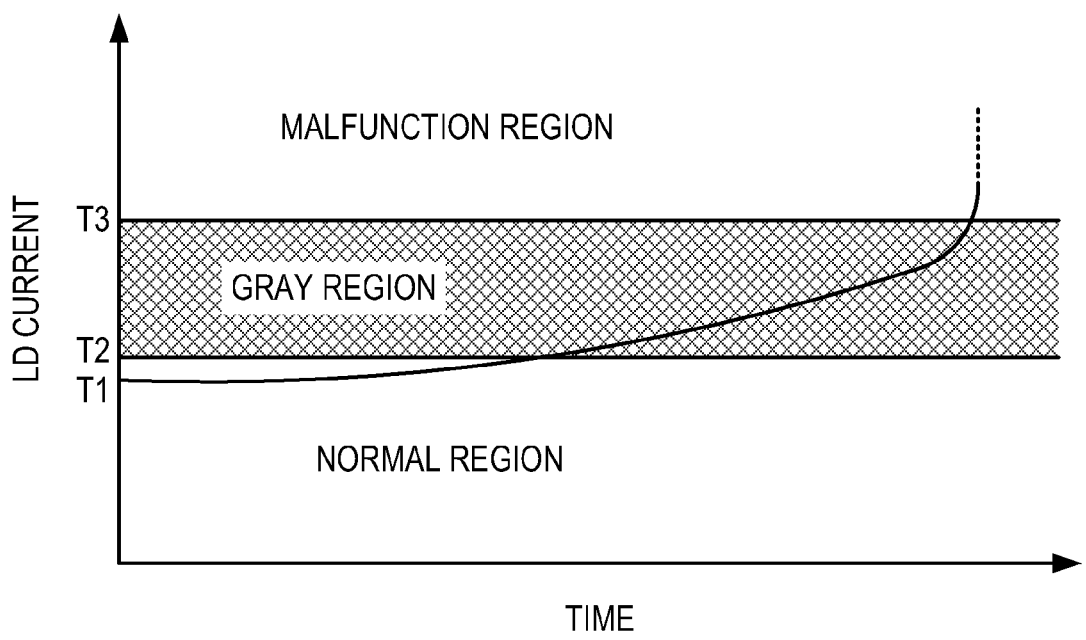
FIG. 6 is a diagram showing the temporal change in the electric current supplied to the laser diode.

FIG. 6 is a diagram showing the temporal change in electric current supplied to a laser diode. The laser diode is supplied with electric current so that the intensity of the laser beam measured by the output beam intensity measurer 56 is held constant. When an LD-pumped solid-state laser to which an electric current of T1 is supplied at the time of delivery is continuously used such as to maintain a constant laser output intensity, the electric current supplied to the laser diode will increase over time. After a certain period of time elapses, as shown by the dotted line, it no longer becomes possible to obtain a laser beam of a certain intensity no matter how much electric current is supplied to the laser diode, as a result of which the laser device is not able to produce its predetermined output. As seen in the diagram, the condition is determined to be normal until the electric current reaches T2, but if it exceeds T3, a malfunction is determined to have occurred. The electric current values T2 and T3 used as the criteria here can, for example, be selected based on experimental data.

The temporal changes shown in FIGS. 5 and 6 depend on the operational environment of the laser device, so that the form of temporal change of the operational data will naturally change according to the various operational environments under which a laser device is operated. FIG. 7 is a diagram showing an example of the operational environment of the laser device. If the operational environments of the laser device are discrete, in other words, if the laser device operates under one of a plurality of preset operational environments, data representing the predicted temporal changes for each operational environment should be recorded. In this case, the values of various operational parameters defining the operational environment are used as indices to find corresponding temporal change data.

Additionally, when using a laser device, there are cases in which it is desirable for a user to be able to freely set the operational parameters so as to obtain desired output characteristics for the laser intensity depending on the environment of usage. In the case where the operational environment is to be capable of being freely set temporal change data corresponding to a number of typical operational environments are recorded as typical temporal change data. When an arbitrary operational environment is set, a similar typical operational environment is retrieved, and the typical temporal change data corresponding to that typical operational environment can be used as temporal change data corresponding to the set operational environment. Additionally, the system may be such as to retrieve a plurality of similar typical operational environments, and to linearly interpolate the typical temporal change data based on the degree of similarity of the set operational environment to the typical operational environments in order to obtain temporal change data corresponding to the set operational environment. Furthermore, the system may be such as to retrieve one or a plurality of similar typical operational environments and apply predetermined conversion rules represented, for example, as computational formulas, to the typical temporal change data corresponding thereto to determine temporal change data corresponding to the set operational environment.

The present invention assumes a system in which the operational parameters defining the operational environment of the laser device can be arbitrarily set by the user, and data indicating the temporal changes in the operational data predicted for the operational environment of the laser device defined by the set parameters are retrieved or generated as described above. By using temporal change data of the operational data, it is possible to check the probability of the seriousness of the problem predicted from the detected operational data based on the time of use of the optical parts, thus preventing mistaken predictions based on incidental factors.

The system may also be such as to determine the necessity of maintenance work based only on the intensity of scattered light, or based on a combination of the intensity of scattered light and other operational data. FIG. 8 is a diagram showing an example of a determination pattern for the necessity of maintenance work. The necessity of maintenance work is indicated for nine determination regions obtained by combining three regions relating to scattered light intensity and three regions relating to LD current value. "No problems" indicates there is no need for maintenance work. "Repair" indicates that repairs are necessary. Additionally, "Caution" and "Warning" indicate that there is no need for immediate repairs, but that maintenance work such as inspections and repairs should be performed within a predetermined period of time. In this case, it is preferable to predict the time until a malfunction is likely to occur in the laser device, and to perform repairs within that time.

The operational data combined with the intensity of scattered light need not be limited to LD current, and may, for example, be the intensity of the output laser beam when the LD current is controlled to be constant, the spectral width of the output laser beam, or the M-squared value which represents the noisiness of the horizontal mode of the laser beam, and determination tables like those shown in Table 8 can be made for each type of operational data. In particular, when the laser beam used in the laser device is a femtosecond pulse laser, combinations using physical values such as pulse width, secondary scattering, tertiary scattering and jitter might be used in addition to the above operational data. Furthermore, three or more elements may be used in combination. In this case, a three-dimensional determination table or four-dimensional or higher determination table would be used.

Figure 9:
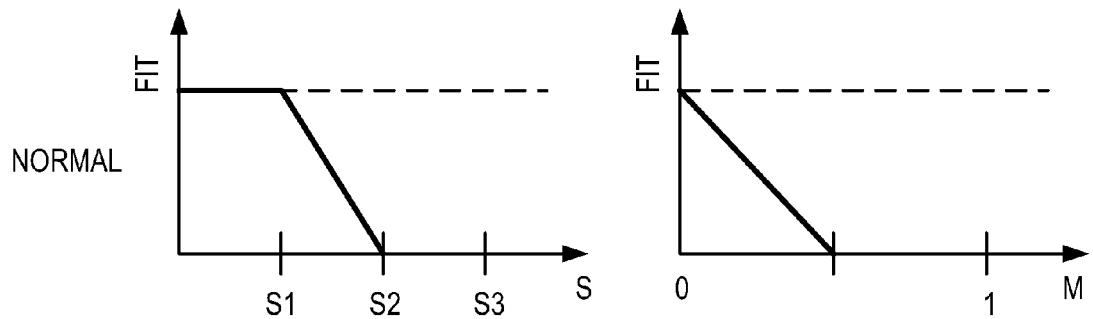
FIG. 9 is a table showing membership functions based on scattered light intensity.
Figure 9:
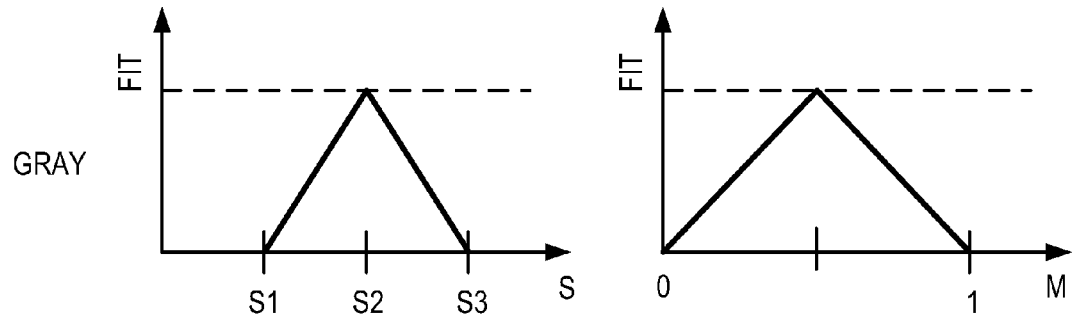
Figure 9:
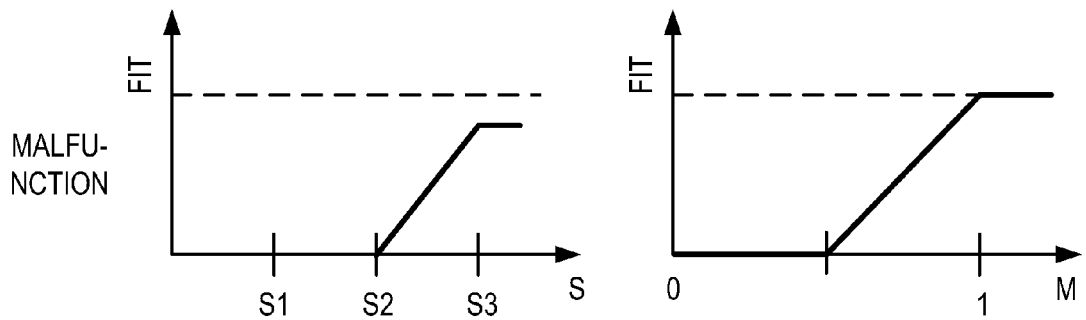

Next, a second determination method shall be described. According to the second determining method, the seriousness of the problem is predicted by performing fuzzy logic based on membership functions defining the relationship between operational data such as scattered light intensity and the seriousness of the problem in the optical part under predetermined operational environments of the laser device. FIG. 9 is a diagram showing membership functions for scattered light intensity. In the membership functions representing the antecedent part of the fuzzy logic, S indicates the intensity of scattered light. Additionally, in the membership function representing the consequent part of the fuzzy logic, M indicates the malfunction risk.

According to the membership function of the antecedent part shown in FIG. 9, the function is fully in the normal region when the intensity of scattered light is smaller than S1. The degree in the normal region decreases and the degree in the gray region increases in the interval of scattered light intensity from S1 to S2. The degree in the gray region decreases and the degree in the malfunction region increases in the interval of scattered light intensity from S2 to S3. The degree is fully in the malfunction region when the scattered light intensity is greater than S3. In the present invention, a MIN-MAX compositional center-of-gravity method is used to compute the malfunction risk M.

Figure 10:
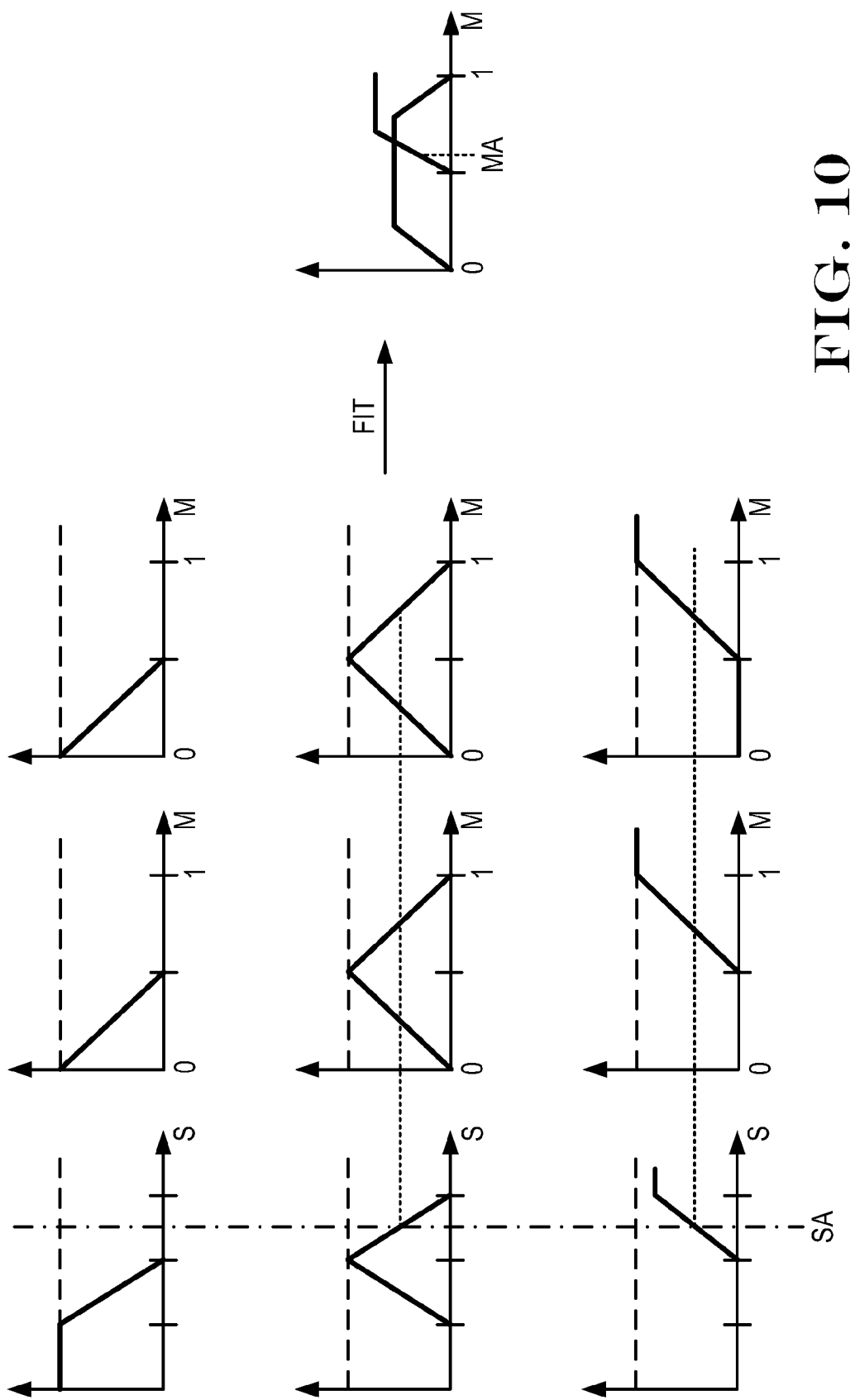
FIG. 10 is a diagram showing an example of the calculation of malfunction risk based on scattered light intensity.

FIG. 10 is a diagram showing an example of the calculation of malfunction risk based on scattered light intensity. The degree of fit to the measured scattered light intensity SA is determined for each of the three membership functions in the antecedent part, and limiting is performed on the membership functions of the corresponding consequent part based on the degree of fit. The limited membership functions can be united by taking the logical sum of the membership functions on which limiting was performed. The center of gravity of the unified membership function is determined, and the malfunction risk predicted for the scattered light intensity is taken as MA. The necessary maintenance work is determined on the basis of this malfunction risk MA.

Figure 11:
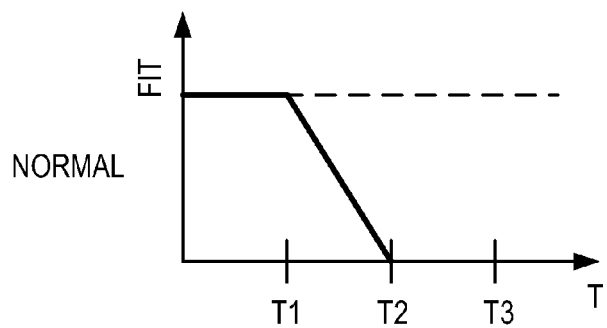
FIG. 11 is a table showing membership functions based on LD current.
Figure 11:
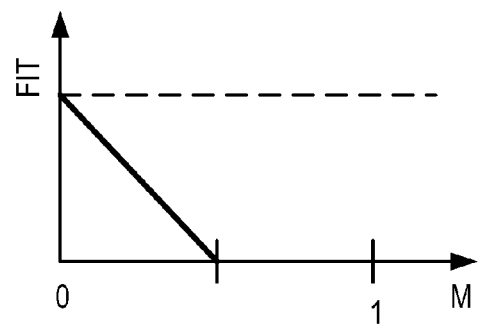
Figure 11:
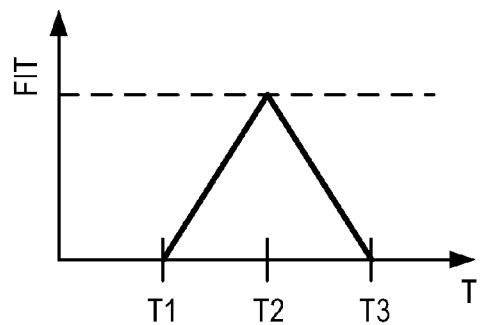
Figure 11:
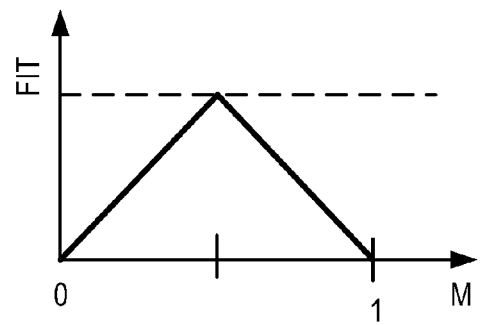
Figure 11:
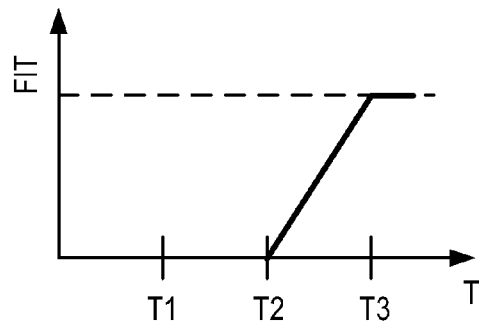
Figure 11:
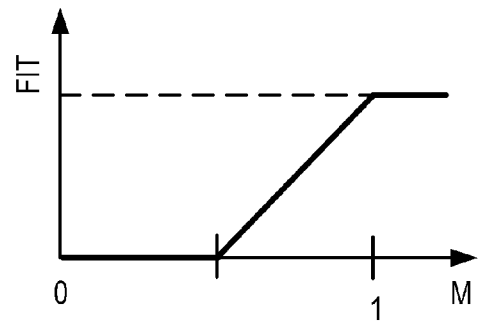

Additionally, the second determination method also may be such as to combine the scattered light intensity with other operational data. FIG. 11 is a diagram showing membership functions relating to LD current. In the membership functions representing the antecedent part of the fuzzy logic, T indicates the value of the LD current. Additionally, in the membership functions representing the consequent part of the fuzzy logic, M indicates the malfunction risk. With regard to the form of the membership function, the same form is taken as that of the membership functions relating to scattered light intensity.

Figure 12:
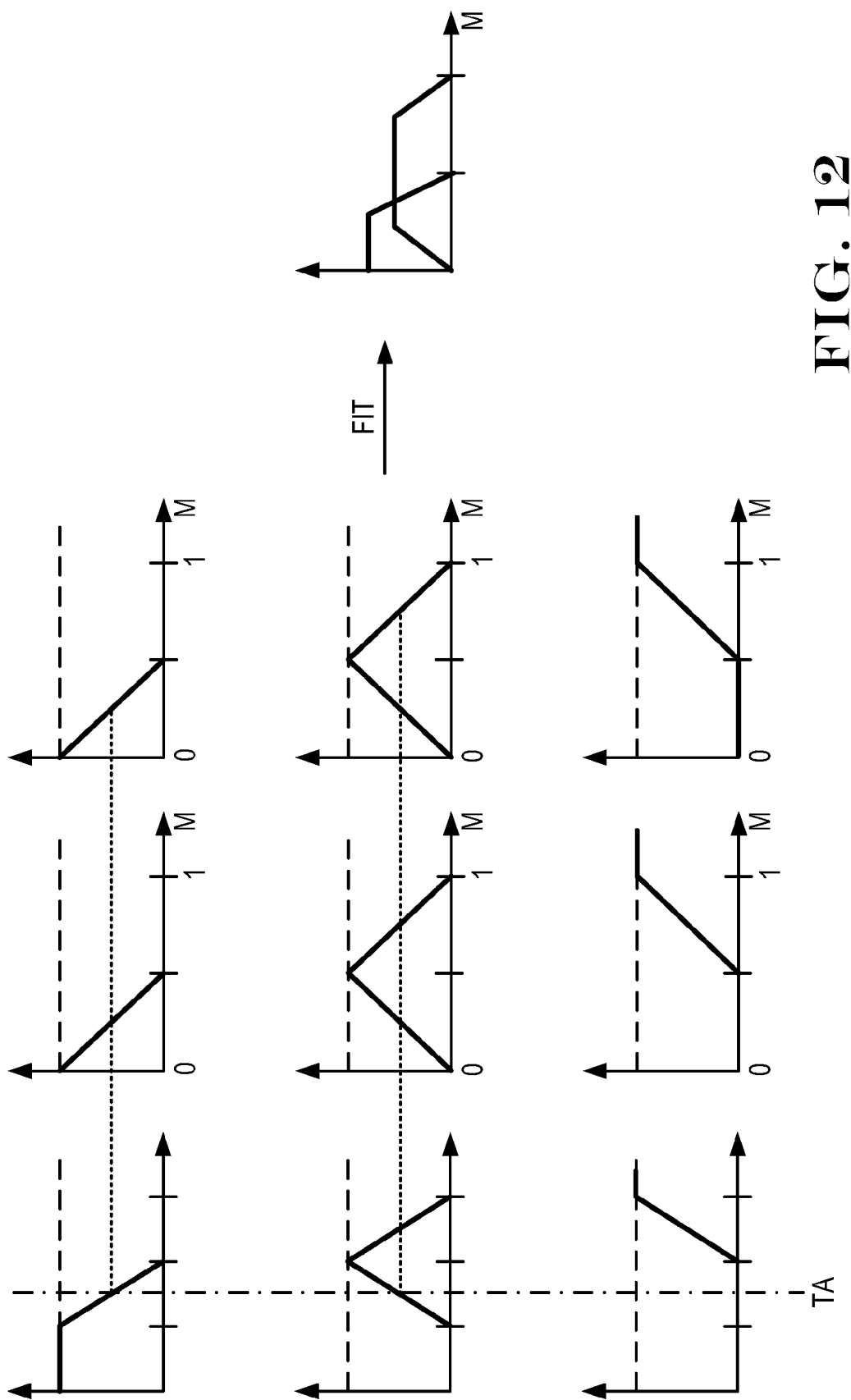
FIG. 12 is a diagram showing an example of the calculation of malfunction risk based on LD current.
Figure 13:
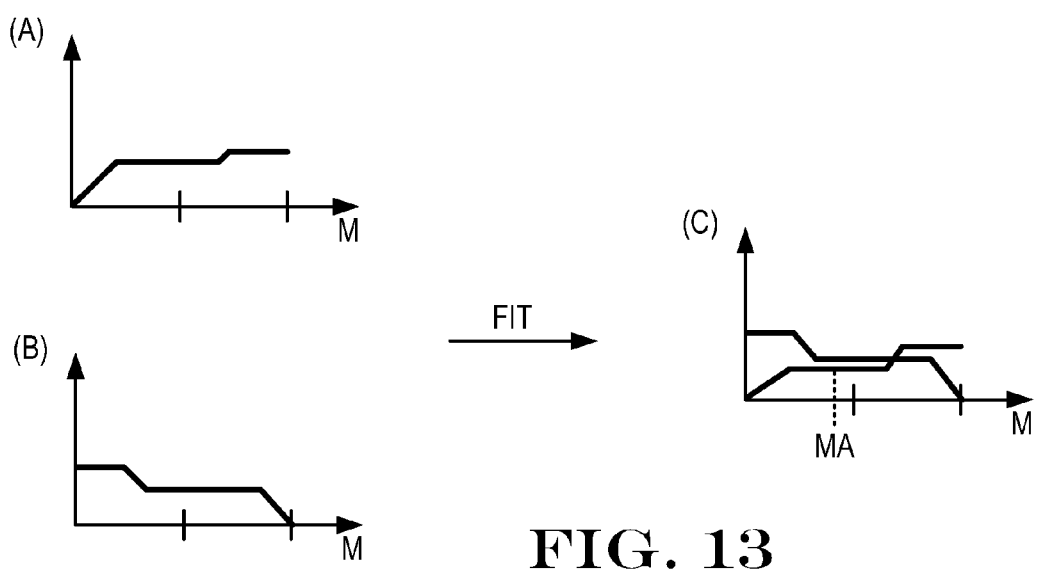
FIG. 13 is a diagram showing the combination of membership functions corresponding to a plurality of operational data.

FIG. 12 is a diagram showing an example of the calculation of malfunction risk based on LD current value. As in the case of scattered light intensity, the limited membership functions are united by determining the degree of fit to the LD current TA and taking the logical sum of the membership functions that have been limited based on the degree of fit. When calculating the malfunction risk by combining the scattered light intensity and the LD current, the logical sum of the united membership functions corresponding to the respective operational data is determined, and the results are further combined. FIG. 13 is a diagram showing the combination of membership functions corresponding to a plurality of operational data. In FIG. 13, (A) is a membership function obtained based on scattered light intensity, and (B) is a membership function obtained based on LD current. The center of gravity of the membership function indicated by (C) obtained by the logical sum of the membership function indicated by (A) and the membership function indicated by (B) is determined and the result is taken as the malfunction risk MA predicted for the scattered light intensity SA and LD current TA. The necessary maintenance work is determined on the basis of this malfunction risk MA.

The membership functions shown in FIGS. 9 and 11 correspond to predetermined operational environments of the laser device, and the form of the membership functions will naturally differ in accordance with various operational environments under which the laser device is operated. As with the temporal change data for the operational data described above, it is likewise preferable, in the case of membership functions, to record typical membership functions and to determine membership functions corresponding to respective operational environments by linear interpolation, or by applying predetermined conversion rules. The present invention assumes a system in which the parameters defining the operational environment of the laser device can be arbitrarily set by the user, and membership functions defining the relationship between the operational data and seriousness of the problem in the optical part in the operational environment of the laser device defined by the set parameters are retrieved or generated.

Figure 14:
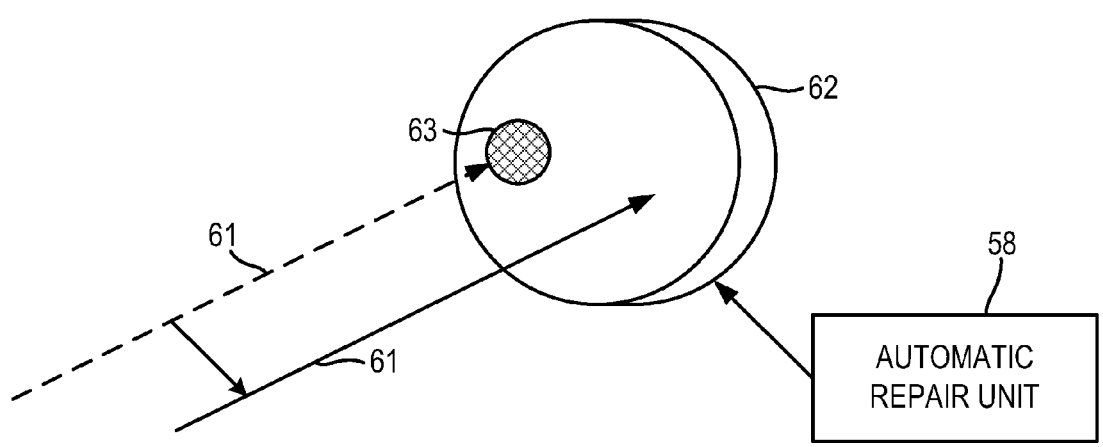
FIG. 14 is a schematic view showing the repair of a laser device by movement of an optical part.

If deterioration of the optical part significantly advances and it is judged that the laser device is in a state of operational anomaly and is in need of repair, the management center is notified that there is an operational anomaly, and when the level of damage is low, the problematic portion is repaired automatically or by remote operation. In the present invention, the laser device can be repaired, for example, by moving the optical part. FIG. 14 is a diagram schematically showing the repair of a laser device by moving the optical part. In the optical part 62 on which the laser beam 61 is incident, a damaged region 63 occurs due to deterioration factors such as mentioned above. When compared with the optical part, the diameter of the laser beam on the surface of the optical part is small, so that the area taken by the damaged region 63 on the surface of the optical part will be relatively small. An automatic repair unit 58 inputted with a control signal ordering a repair will move the optical part 62 in a direction perpendicular to the direction of irradiation of the laser beam, so as to displace the area on which the laser beam 61 is incident on the optical part 62 from the damaged region 63. As a result, the laser device overall can be returned to working order.

With regard to the movement of the optical part, the structure may be such as to move the optical part a specific, predetermined distance. Additionally, the structure may be such as to move the optical part while the scattered light intensity is being measured by the scattered light sensor, and to stop the movement when the scattered light intensity becomes a predetermined threshold value or less. As a result, it is possible to reliably irradiate the laser beam on a portion of the optical part other than the damaged region. The above repair method is preferably applied to an optical part to which the laser beam does not need to be irradiated on a central portion.

Figure 15A:
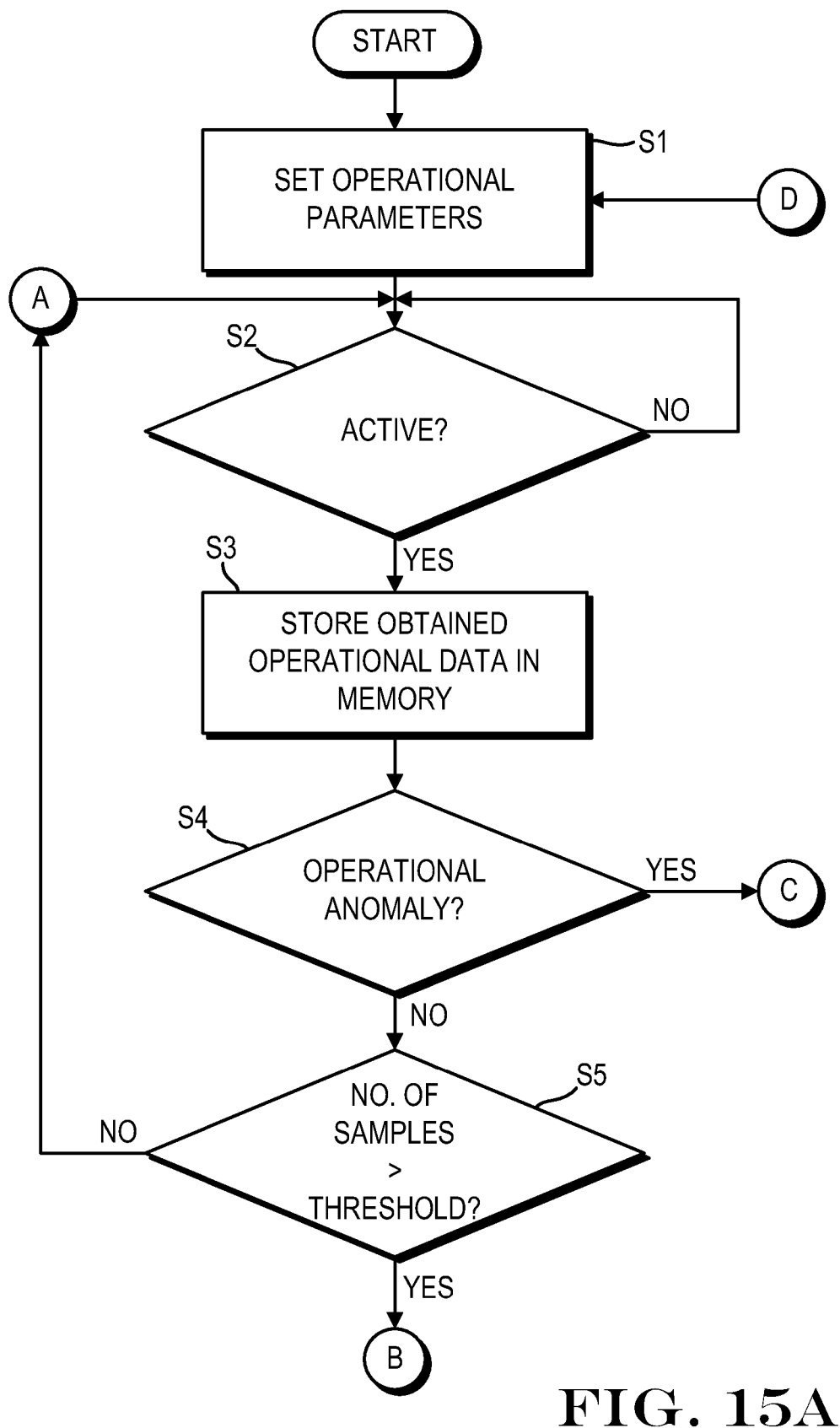
FIG. 15 is a flow chart showing a problem diagnosis method and problem repair method according to the present invention.
Figure 15B:
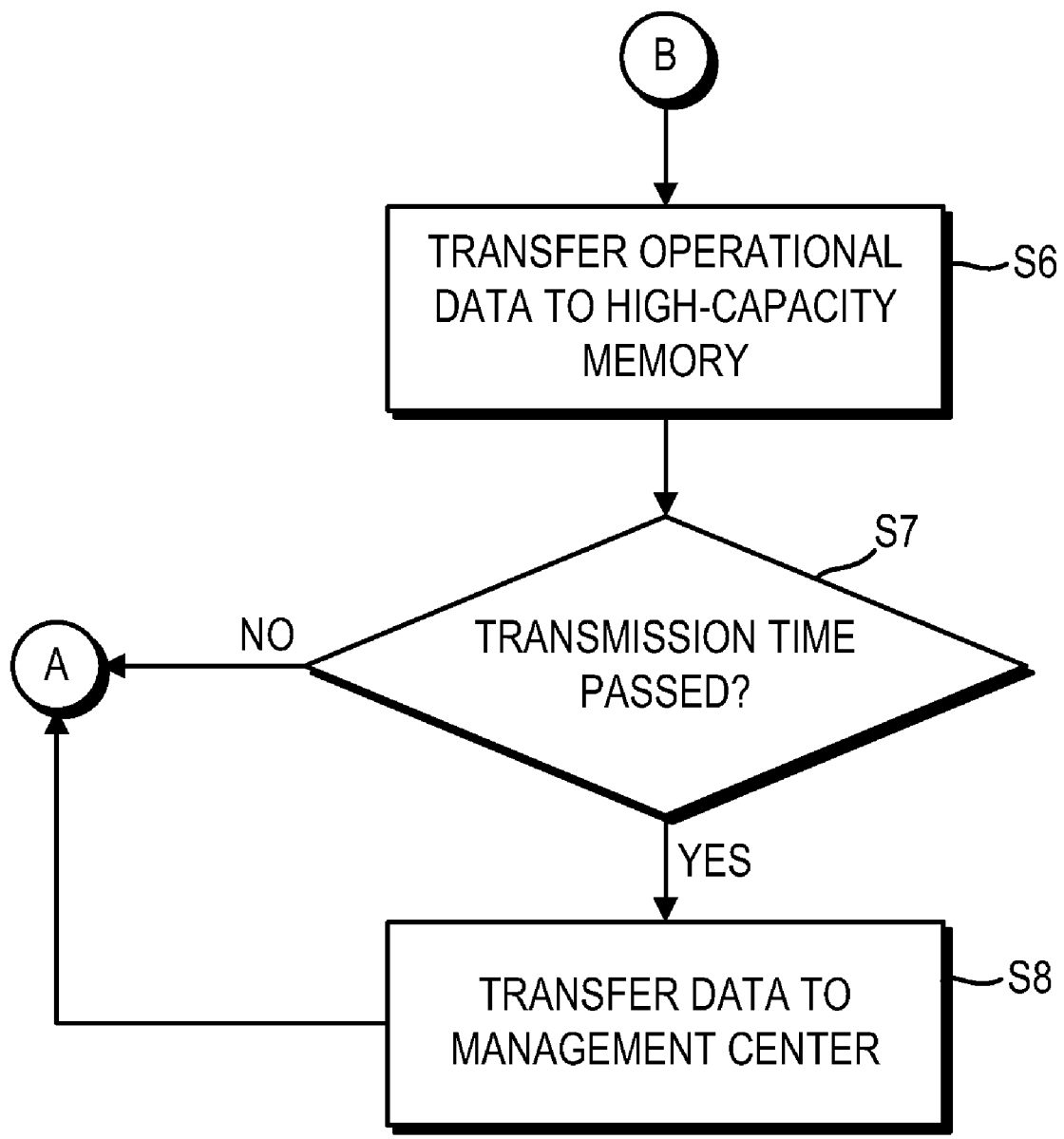
Figure 15C:
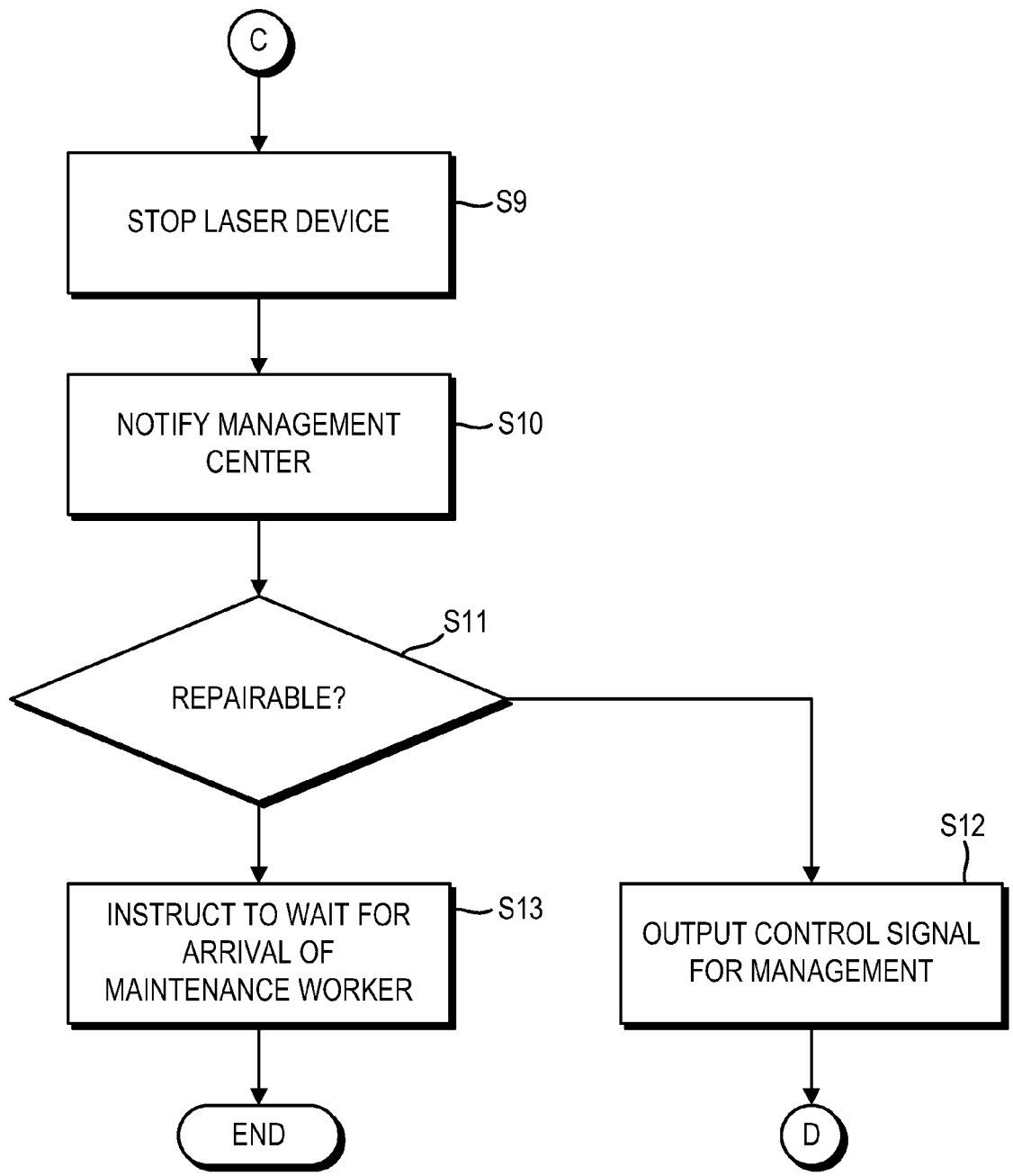

Next, the problem diagnosis method and problem repair method shall be described in detail. FIG. 15 is a flow chart indicating a problem diagnosis method and problem repair method according to the present invention. With regard to these methods, they can be achieved by storing software programs consisting of modular programs for executing each of the steps indicated in the flow charts in the memory 10, then executing the program. When the laser device is activated, the user stores desired operational parameters in the memory 10 (step S1). Examples of operational parameters for defining the operational environment of the laser device include output optical energy, pulse repetition number and pulse width. Once the operational parameters are set, the laser device will be assumed to be under the same operational environment until the operational parameters are next modified, so that the same standards will be applied to make judgments on operational anomalies. That is, temporal change data or membership functions for operational data such as scattered light intensity are retrieved from a database depending on the operational environment set by the user, and if necessary, data corresponding to the set operational environment is generated based on the retrieved data.

When the operational environment of the laser device has been set, a judgment is made as to whether or not the laser device is active (step S2). If the laser device is not active, this judgment step is repeated. That is, the process does not progress to the next step until the laser device is found to be active. If the laser device is found to be operational, the active data obtained from the various sensors attached to the laser device are stored in the memory 10 (step S3).

When the operational data of the laser device are stored, the MPU 9 references temporal change data, or executes fuzzy logic based on the operational data such as a scattered light intensity stored in the memory 10, to thereby predict the seriousness of the problem in the optical part. The MPU 9 determines the maintenance work that is necessary and whether or not the laser device is in an anomalous state based on this predicted seriousness of the problem (step S4). Additionally, the MPU 9 prepares problem information specifying the predicted seriousness of the problem, the optical part in which the problem occurred, and the type of maintenance work that is considered necessary, and stores this information in the memory 10 or a high-capacity memory device 11.

If the laser device is determined not to be in an anomalous operational state in step S4, it is determined whether or not the number of samples stored in the memory 10 is greater than or equal to a predetermined threshold value (step S5). If the number of samples has not reached a predetermined threshold value, the procedure returns to step S2. On the other hand, if the procedure has reached the predetermined threshold value, the operational parameters and operational data stored in the memory 10 are transferred and stored in the high-capacity memory device 11 (step S6). In this embodiment, the structure is such that when the number of samples stored in the memory 10 exceeds a predetermined threshold value, data is transferred from the memory to the high-capacity memory device, but the structure may, for example, be such that the data is transferred when the stored data reaches a limit capacity of the memory 10. Furthermore, the structure may also be such that a signal indicating that the laser device is no longer active is used as a trigger to transfer data.

When the operational data are transferred to the high-capacity memory device, it is determined whether the current time has passed a predetermined transmission time (step S7). If the predetermined transmission time has not passed, then the procedure is returned to step S2. Additionally, if the predetermined transmission time has passed, the MPU 9 transmits all or a portion of the operational data stored in the high-capacity memory device 11 through a communication control portion 12 to a management center connected to an external communication network 13 (step S8). With regard to transmission of the operational data to the management center, the structure may be such as to separately activate a transmission time monitoring program, and to interrupt the program executing the algorithm shown in FIG. 15 upon reaching a predetermined time, to transmit the operational data. For example, in the case of a medical laser device, it is preferable to transmit the operational data at a time when medical activity is not being performed.

If the device is determined to be in an anomalous operational state in step S4, the operation of the laser device is stopped, if necessary by controlling the power supply portion 3 (step S9). Additionally, the management center is notified that the laser device is in an anomalous operational state, and the problem information is transmitted to the management center (step S10).

After notifying the management center that an operational anomaly has occurred, the MPU 9 determines whether automatic repairs are possible based on the form of the operational anomaly or the location where the anomaly occurred (step S11). If repairs are possible, it outputs a control signal ordering repairs to one or a plurality of constituent parts in the laser device (step S12). This automatic malfunction repair can be performed, for example, by moving the optical part to displace the position where the laser beam is irradiated from the damaged portion, as described above.

Additionally, if necessary after the repairs have been completed, the emergency suspension of the laser device can be undone and the laser device restarted. Examples of cases in which restarting will be possible include cases in which the repairs are completed, or the operational data indicating the anomaly were accidental and due to noise from the external environment. However, if the operational data indicating the anomaly are accidental, it is preferable for a maintenance worker to inspect the part that detected the operational data.

If it is determined in step S11 that repairs are not possible, a message is displayed, for example using a display provided on the laser device, and the user is instructed to wait for a maintenance worker to arrive (step S13). If the level of the operational anomaly is low, then the operation of the laser device may be continued, in which case the process would return to step S2 to continue monitoring the laser device.

The present invention should not be construed as being in any way limited by the laser device problem diagnosis method and repair method explained by the above embodiments, which are intended only to illustrate possible examples. The technical scope of the present invention is defined in the claims, and various design modifications are naturally possible within the technical scope recited in the claims.

For example, the determination of whether or not an operational anomaly has occurred in the laser device may be made within the laser device as described above, or may be made in the management center based on transmitted problem information. Additionally, the same applies to the determinations of whether the device can be repaired and whether the device can be restarted. The determination by the management center can be performed automatically using a computer, or may be determined by an expert observing the data.

The invention claimed is:

1. A problem diagnosis method for a laser device that includes a beam generator outputting a laser beam, an optical sensor receiving a scattered laser beam generated by an optical part disposed inside or outside of the beam generator and outputting electrical signals corresponding to an intensity of the scattered laser beam, and a prediction control unit predicting a seriousness of a problem which occurs on the optical part based on the electrical signals outputted from the optical sensor, the problem diagnosis method comprising the steps of:

predicting a temporal change in the intensity of the scattered laser beam generated by the optical part based on operating conditions of the laser device;

measuring the intensity of the scattered laser beam generated by the optical part;

referring to data indicating the temporal change in the intensity of the scattered laser beam predicted under the operating conditions, and predicting the seriousness of the problem occurring on the optical part by comparing the intensity of the scattered laser beam that is measured with the data indicating the temporal change in the intensity of the scattered laser beam that is predicted; and determining what kind of maintenance work is necessary based on the seriousness of the problem predicted.

2. The problem diagnosis method for a laser device in accordance with claim 1, further comprising the steps of:

predicting a temporal change in different operational data of the optical part other than the intensity of the scattered laser beam based on the operating conditions of the laser device;

measuring the different operational data of the optical part by using a sensor disposed so as to measure the different operational data; and referring to data indicating the temporal change in the different operational data predicted under the operating conditions, and predicting the seriousness of the problem occurring on the optical part by comparing the different operational data measured using the sensor with the data indicating the temporal change in the different operational data predicted under the operating conditions;

wherein necessary maintenance work is determined based on the seriousness of the problem derived from the intensity of scattered light that is measured and the seriousness of the problem derived from the different operational data that is measured.

3. The problem diagnosis method for a laser device in accordance with either claim 1 or 2, further comprising the step of:

identifying operating conditions of the laser device based on one or a plurality of operational parameters relating to the laser device which are set by a user of the laser device, wherein, in order to predict temporal changes in one or a plurality of operational data including at least the intensity of a scattered laser beam, data indicating the temporal changes in the one or the plurality of operational data are retrieved or generated based on the operating conditions of the laser device identified based on the one or the plurality of operational parameters relating to the laser device.

4. A problem diagnosis method for a laser device in accordance with claim 1, further comprising:

a step of reporting problem information to a management center through a network.

5. A problem diagnosis method for a laser device in accordance with claim 4, further comprising a step of instructing a maintenance worker at the management center to perform inspections or repairs based on the problem information.

6. A problem repair method for a laser device that includes a beam generator outputting a laser beam, an optical sensor receiving a scattered laser beam generated by an optical part disposed inside or outside of the beam generator and outputting electrical signals corresponding to an intensity of the scattered laser beam, a prediction control unit predicting a seriousness of a problem which occurs on the optical part based on the electrical signals outputted from the optical sensor, and an automatic repair unit receiving control signals outputted from the prediction control unit and moving the optical part based on the control signals, the problem repair method comprising the steps of:

predicting a temporal change in the intensity of the scattered laser beam generated by the optical part based on operating conditions of the laser device;

measuring the intensity of the scattered laser beam generated by the optical part;

referring to data indicating the temporal change in the intensity of the scattered laser beam predicted under the operating conditions and predicting the seriousness of the problem occurring on the optical part by comparing the intensity of the scattered laser beam that is measured with the data indicating the temporal change in the intensity of the scattered laser beam that is predicted;

determining what kind of maintenance work is necessary based on the seriousness of the problem that is predicted; and moving the optical part such that the intensity of the scattered laser beam generated by the optical part decreases, based on the maintenance work that is determined to be necessary.

7. A problem repair method for a laser device in accordance with claim 6, wherein said optical part is moved until the intensity of scattered light generated by the optical part becomes less than or equal to a predetermined threshold value.

* * * * *